United States Patent [19]

Wheeler et al.

[11] Patent Number: 5,258,519

[45] Date of Patent: Nov. 2, 1993

[54] DIHYDROPYRIDINE VASODILATORS AGENTS

[75] Inventors: Thomas N. Wheeler, Raleigh; Terrence P. Kenakin, Durham, both of N.C.

[73] Assignee: Glaxo Inc., Research Triangle Park, N.C.

[21] Appl. No.: 805,604

[22] Filed: Dec. 10, 1991

Related U.S. Application Data

[62] Division of Ser. No. 613,182, Nov. 13, 1991, Pat. No. 5,100,892.

[51] Int. Cl.$^5$ ................. C07D 213/64; C07D 213/55; C07D 213/57; A61K 31/435
[52] U.S. Cl. ..................................... 546/261; 546/263; 546/288; 546/322; 544/238
[58] Field of Search ............... 546/288, 261, 257, 263; 514/318

[56] References Cited

U.S. PATENT DOCUMENTS

| | | |
|---|---|---|
| 4,532,248 | 6/1985 | Franckowiak et al. ............ 514/302 |
| 4,686,229 | 8/1987 | Rosentreter et al. ............ 514/332 |
| 4,707,470 | 11/1987 | Meyer et al. ............ 514/222 |
| 4,876,254 | 10/1989 | Franckowiak et al. ............ 514/252 |
| 4,876,255 | 10/1989 | Franckowiak et al. ............ 514/252 |
| 4,898,865 | 2/1990 | Franckowiak et al. ............ 514/252 |

FOREIGN PATENT DOCUMENTS

0174654 9/1985 European Pat. Off. ............ 546/194

Primary Examiner—Alan L. Rotman
Attorney, Agent, or Firm—David J. Levy; Charles T. Joyner

[57] ABSTRACT

Compounds of the following formula (I):

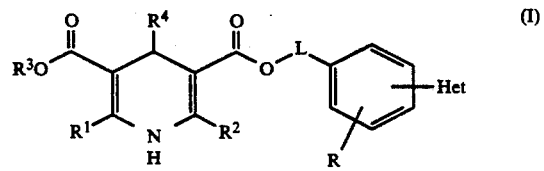

where $R^1$ and $R^2$ are alkyl or cycloalkyl, which may be substituted, $R^4$ is aryl such as phenyl which may be substituted, L is a direct bond or an oxygen containing linking group, R is a hydrogen, alkyloxy, alkyl, halogen or haloalkyl and Het is a pyridinyl or pyridazinyl group. The compounds can be used antihypertensives or myocardial relaxants. Also part of the invention are pharmaceutical compositions, intermediates and methods of synthesis.

1 Claim, No Drawings

DIHYDROPYRIDINE VASODILATORS AGENTS

This is a division of U.S. Ser. No. 07/613,182, filed Nov. 13, 1991 which is now U.S. Pat. No. 5,100,892.

BACKGROUND OF THE INVENTION

Vasodilators such as nifedipine have been used to open the vascular system and permit the freer flow of blood. Coronary vasodilators are thus useful in the treatment of angina pectoris. Peripheral vasodilators find utility in lowering blood pressure and thus are used in the treatment of hypertension. However, peripheral vasodilation may result in reflex tachycardia whereby the heart rate is speeded up to compensate for, and thus neutralize the effect of, the loss of blood pressure. An object of the invention is a peripheral vasodilator useful in treating hypertension which does not result in reflex tachycardia or other undesireable actions of the heart.

Milrinone is a bipyridine inotropic agent which has been investigated for use in improving cardiac function in patients with congestive heart failure. The primary mechanism of this agent has been thought to be improvement in left ventricular systolic function whereby the contractile forces in the heart are strengthened. However, it is recognized by E. S. Monrad et al in Circulation, Vol. 70, No. 6, pp 1030-1037 (1984) that improved diastolic function may contribute to the beneficial effect of this drug. Milrinone and its use as a cardiotonic, e.g. in treating congestive heart failure, is taught in U.S. Pat. Nos. 4,313,951 and 4,413,127. It is also an object of this invention to provide a "lusitropic" agent useful in the treatment of congestive heart failure which acts through the mechanism of improved myocardial relaxation in the diastolic portion of the heart rhythm.

Dihydropyridines having ester moieties at the 3-position are taught in European Patent 291,799 and German DE 3,712,371 and DE 3,724,909.

SUMMARY OF THE INVENTION

Dihydropyridine compounds of formula (I) and their use in treating hypertension and other cardiac conditions such as congestive heart failure in mammals, e.g. man, as well as pharmaceutical compositions, novel intermediates and processes of synthesis are aspects of the present invention.

DETAILED DESCRIPTION OF THE INVENTION

This invention relates to novel compounds and pharmaceutical compositions thereof. In particular, the subject chemical compounds are 4-aryl-1,4-dihydropyridines of the following formula (I):

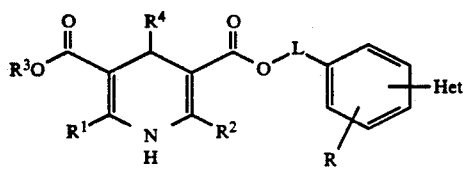

wherein:
R$^1$ and R$^2$ are independently lower alkyl or cycloalkyl, optionally substituted by halogen, aryl, heteroaryl, carboxy, alkyloxy, alkyloxycarbonyl, acyloxy, hydroxy, amino, alkylamino, or dialkylamino;

R$^3$ is alkyl, cycloalkyl, alkenyl, or cycloalkenyl;

R$^4$ is aryl optionally substituted by 1-5 groups selected from alkyl, halogen, cyano, nitro, haloalkyl, amido, sulfonamido, alkylsulfonyl, carboxy, alkyloxycarbonyl, alkyloxy, haloalkyloxy, aralkyloxy, alkylthio, haloalkylthio, or aralkylthio groups;

L is a direct bond or a linking group of the following formula (II) or (III):

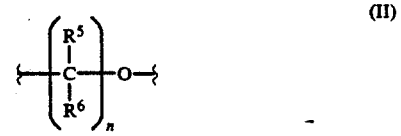

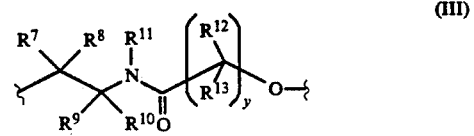

in which:
R$^5$–R$^{13}$ may be independently hydrogen or lower alkyl;
n is 1-6;
y is 1-6;
R is hydrogen, alkyloxy, alkyl, halogen or haloalkyl;
Het is a heterocyclic moiety of the following formula Het-A or Het-B:

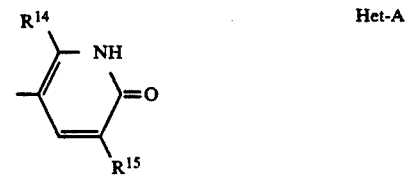

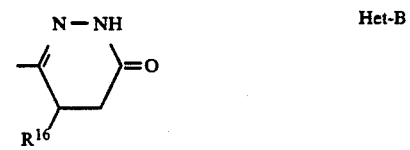

in which:
R$^{14}$ is hydrogen or lower alkyl;
R$^{15}$ is hydrogen or cyano; and
R$^{16}$ is hydrogen or lower alkyl, with the proviso that when L is a direct bond, R$^{16}$ is not hydrogen, and the pharmaceutically acceptable salts thereof.

As used herein, "lower alkyl" per se or as part of another group such as lower alkoxy may be about 1 to 3 carbons, straight or branched chain; "alkyl" may be about 1 to 6 carbons, straight or branched chain; "cycloalkyl" may be about 3 to 7 carbons; "independently" indicates that members, where two or more are present, need not be identical e.g. there may be 3 different R$^5$ groups in a molecule where n=3; "halogen" is fluoro, chloro, bromo, or iodo; the L group is attached as shown in the definitions, i.e. the carbon carrying R$^5$ and R$^6$ in formula (II) is attached to the carboxylate oxygen in formula (I) and the oxygen in formula (II) is attached to the phenyl ring as indicated in formula (I). Similarly, the carbon bearing $R^7$ and $R^8$ in formula (III) is attached to the oxygen atom of the carboxylate group of formula (I) and the ether oxygen in (III) is attached to the phenyl ring indicated in formula (I). The point of attachment of Het-A and Het-B is the 5-position and 6-position, respectively with the pendant bond to the phenyl ring being shown in the formulae depicted above as Het-A and Het-B. Het as well as R can be attached to the phenyl ring at any of the open ortho, meta or para positions.

In more detail, $R^1$ and $R^2$ may be lower alkyl such as methyl or cycloalkyl such as cyclohexyl with or without substitution which may include one or more, e.g. 1 or 2, of halogen, aryl such as phenyl, heteroaryl such as pyridino or indolino, carboxy, alkyloxy such as methoxy, alkyloxycarbonyl such as methoxycarbonyl, acyloxy such as alkylcarbonyloxy, hydroxy, amino, alkylamino such as methylamino, or dialkylamino such as dimethylamino.

$R^3$, in more detail may be alkyl such as methyl or ethyl, cycloalkyl such as cyclohexyl, alkenyl of about 2 to 6 carbons such as vinyl or allyl, or cycloalkenyl of 4 to 7 carbons such as 2-cyclohexenyl.

$R^4$, in more detail, is phenyl or naphthyl with or without substitution by 1-5 groups including alkyl such as methyl; halogen particularly including chloro; nitro; haloalkyl including trifluoromethyl and 2,2,2-trichloroethyl; amido ($-CONH_2$); sulfonamido ($-SO_2NH_2$); alkylsulfonyl such as methylsulfonyl; carboxy; alkyloxycarbonyl such as methoxycarbonyl; alkyloxy such as methoxy, haloalkyloxy such as trifluoromethoxy, aralkyloxy such as benzyloxy; alkylthio such as methylthio; haloalkylthio such as chloromethylthio; and aralkylthio such as benzylthio.

$R^5-R^{13}$, in more detail are hydrogen or methyl.

The integer represented by n may, in particular, be 3 and the integer for y may be 1.

R may be hydrogen, halogen, alkyloxy such as methoxy, alkyl such as methyl and haloalkyl such as trifluoromethyl or 2,2,2-trifluoroethyl. R may be attached at the ortho, meta or para positions relative to the —L— moiety. In particular, R may be attached ortho to the —L— moiety.

$R^{14}$ may, in particular, be methyl and $R^{15}$ may be cyano. $R^{16}$ may, in particular, be methyl.

Particular salts of the compounds of formula (I) include base-addition salts when $R^1$, $R^2$ or $R^4$ have a carboxy substituent and acid-addition salts when $R^1$ or $R^2$ have an amino or substituted amino. Suitable base cations include the alkali metals such as sodium and the alkaline earth metals such as magnesium as well as organic bases cations such as amines, e.g. triethylammonium. A wide variety of acids may be employed to form such salts and representative examples of such acids include inorganic acids, e.g. hydrochloric acid, hydrobromic acid, hydroiodic acid, phosphoric acid, nitric acid, and sulfuric acid; and organic acids, e.g. maleic acid, fumaric acid, acetic acid, benozoic acid, p-toluenesulfonic acid, tartaric acid, citric acid, succinic acid, lactic acid, and propionic acid. These acid or base addition salts are prepared by conventional methods. Compounds of the formula (I) may also exist as a solvate; e.g. a hydrate or hemihydrate, and such are within the scope of the invention.

Preferred compounds of this invention are those of formula (I) with one or more of the following definitions: $R^1$ and $R^2$ are each methyl; $R^3$ is methyl, ethyl, or isopropyl; $R^4$ is phenyl substituted by nitro and/or halo, e.g. 2-nitro, 3-nitro, 2,3-dichloro, or 2-chloro-3-nitrophenyl; L is a linking group of the formula (III) with $R^7-R^{13}$ all hydrogen and y=1; Het is a heterocyclic moiety of the type Het=A and $R^{14}$ is a methyl group and $R^{15}$ a cyano group.

The compounds of the formula (I) may have, e.g. depending on the definition of $R^5-R^{10}$ and $R^{12}$, one or more asymmetric carbon atoms in their structure, and consequently they may exist in different optical isomeric forms or mixtures, e.g. racemates or mixtures of diasteromers. In particular, the chirality at $C_4$ of the dihydropyridine in formula (I) is always present and additional chiral centers may result from substitution in the link, L. Enantiomeric forms and mixtures of such forms may be obtained separately by application of methods of resolution known to those skilled in the art such as, for example, salt formation of the dihydropyridine monocarboxylic acid with an optically active base followed by selective crystallization or chromatography. This diastereomeric salt is then converted back to the enantiomeric dihydropyridine acid which is then converted to compounds of the formula (I). All stereoisomeric forms of the compounds of formula (I), including mixtures of diastereomers, pure diastereomers, enantiomers and mixtures thereof are understood to be within the scope of this invention.

The compounds of formula (I) in which the linking moiety L is of the formula (II) may be prepared as shown in Scheme I. In Scheme I the various R groups, Het and n are as defined above for formula (I). In the compound of formula (IV), X is a leaving group such as hydroxy whereby the starting material is a carboxylic acid.

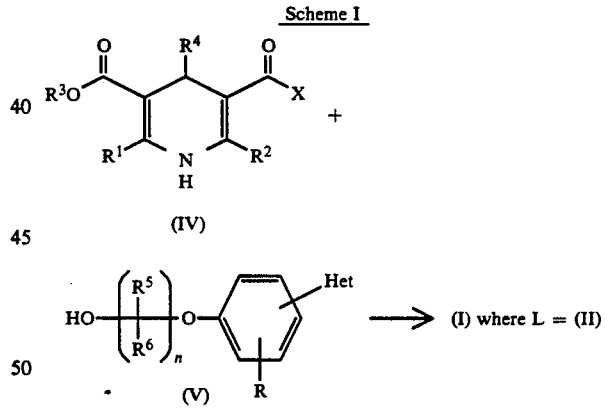

Scheme I

When X=OH, the reaction illustrated in Scheme I may be executed by treating a mixture of compounds (IV) and (V) in the presence of an inert solvent with a suitable dehydrating agent such as DCC and optionally a catalyst. With other leaving groups as X, a dehydrating agent may not be necessary. Suitable solvents for the coupling reaction are tetrahydrofuran, acetonitrile, benzene, toluene, methylene chloride, chloroform, and DMF. The preferred conditions for effecting the reaction shown in Scheme I is to use DCC as the dehydrating agent, 4-dimethylaminopyridine as a catalyst, DMF as the solvent, and a temperature in the range of 25° C. to 100° C.

When X is other than OH in formula (IV), the reaction between (IV) and the alcohol of formula (V) is preferably effected in the presence of an inert solvent, such as an aromatic hydrocarbon, e.g. benzene or toluene, an ether, such as diethyl ether or tetrahydrofuran, or a halogenated solvent such as methylene chloride. The reaction may be carried out over a wide range of temperatures, with a particular temperature range being 0° C. to 25° C.

The compound of formula (IV) where X is OH may be converted to a suitably reactive derivative where X is a leaving group other than —OH. Suitably reactive derivatives for formula (IV) include: acid halides, such as the acid chloride; mixed anhydrides of the carboxylic acid with another organic acid such as acetic acid, propionic acid, or pivalic acid; acyl imidazoles; and active esters of the carboxylic acid, such as the 4-nitrophenyl ester. The mixed anhydrides may be prepared by treating (IV), X=OH, with carboxylic acid chlorides, e.g. acetyl chloride, pivaloyl chloride, or isobutoxycarbonyl chloride in the presence of a proton acceptor and an inert solvent. Suitable proton acceptors include both organic bases such as triethylamine or 4-dimethylaminopyridine and inorganic bases such as anhydrous potassium carbonate. The acid halides may be prepared by reacting (IV), X=OH, with a suitable halogen compound such as thionyl chloride, oxalyl chloride, or phosphorus pentachloride in the presence of small amounts of DMF or pyridine. The acyl imidazoles are prepared by treating (IV), X=OH, with carbonyl diimidazole. Suitable solvents for forming reactive derivatives for formula (IV) from (IV) where X=OH include diethyl ether, tetrahydrofuran, aromatic hydrocarbon solvents such as benzene or toluene, methylene chloride, or chloroform. Thus X may be specifically hydroxy, chloro, isobutyloxycarbonyloxy, imidazole, or 4-nitrophenyl.

Many of the compounds of formula (IV) employed as starting materials in Scheme I are either already known or may be prepared by known methods, for example as described in European Patent application 273,349 or in U.S. Pat. No. 4,595,690. A general approach to the synthesis of compounds of the formula (IV) with X=OH is shown in Scheme II below. Scheme II is a modification of the well-known Hantzsch dihydropyridine syntheses (A. Hantzsch, Liebigs Ann. Chem. 215 (1882)1), which has been reviewed by D. M. Stout et al in Chem. Rev. 82, 223-242 (1982).

Scheme II

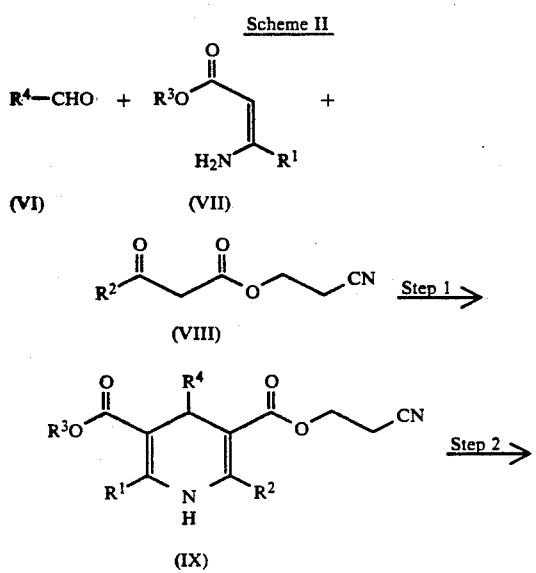

(VI) (VII) (VIII)

(IX)

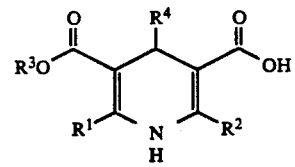

(IV, X = OH)

Starting materials (VI), (VII), and (VIII) are either known, commercially available materials or may be readily prepared by one skilled in the art of organic synthesis with $R^1$, $R^2$, $R^3$ and $R^4$ being as defined in formula (I). Step 1 in Scheme II is conducted by refluxing a mixture of (VI), (VII), and (VIII) in a molar ratio of about 1:1:1 in an alcoholic solvent, e.g. ethanol or isopropanol. Step 2 is effected by stirring the dihydropyridine of formula (IX) in an aqueous base e.g. aqueous sodium hydroxide in a temperature range of about 0° C. to 25° C.

Compounds of the formula (IV) where X=OH exist as optical isomers. It is frequently desirable for reasons of enhanced biological activity to separate compounds of the formula (IV) into the individual pure enantiomers, see K. Muto et al, Arzneim-Forsch., 38, 1988, 1662-1665 and references therein. The resolution of compounds of compounds as in formula (IV) has been described by F. Shibanuma et al in Chem. Pharm. Bul., 28(9), 2809-2812 (1980) and in Eur. Pat. Appl. 249,245. Using analogous methods, compounds of the formula (IV) where X=OH have been resolved and the pure enantiomers have been converted to compounds of the formula (I).

In Scheme I compounds of the formula (V) may be prepared as shown in Scheme III:

Scheme III

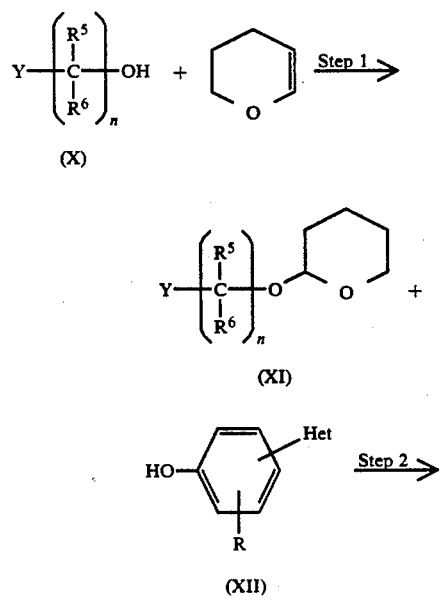

-continued
Scheme III

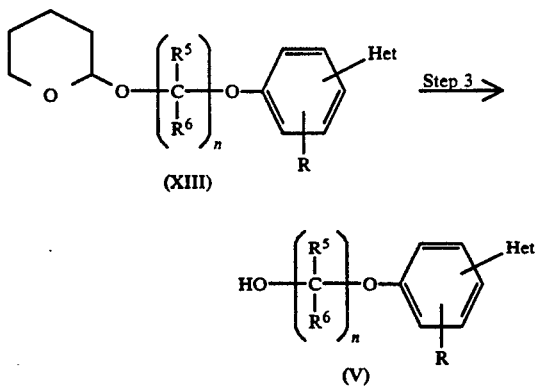

In compounds of formula (X), Y represents a leaving group at one end of the chain that is reactive toward displacement by nucleophiles. Suitable Y groups include halogen and the p-toluenesulfonate, p-nitrobenzenesulfonate, methanesulfonate, and trifluoromethanesulfonate esters. In Scheme III, $R^5$, $R^6$, n, R and Het are as defined for formula (I). The compounds of formula (X) are either known or may be prepared from the corresponding haloalkanols or alkyl diols by conventional methods well known to those skilled in the art.

Step 1 in Scheme III is effected by reacting a compound of formula (X) with dihydropyran in the presence of a suitable catalyst and a solvent to give the THP-protected alcohol (XI). Suitable catalysts for this reaction are: p-toluenesulfonic acid, pyridinium p-toluenesulfonate or an ion exchange resin containing —$SO_3H$ substituents, such as amberlyte H-15. Appropriate solvents for the reaction are the halogenated hydrocarbon solvents such as methylene chloride or chlorform.

Step 2 in Scheme III is executed by reacting a phenol of the formula (XII) with a compound of the formula (XI) in the presence of a suitable base and a solvent. The base used in Step 2 of Scheme III is dependent upon the definition of Het. If Het is of the formula Het-B, suitable bases are sodium hydride, potassium carbonate, potassium t-butoxide, and similar non-nucleophilic basic reagents. If Het is of the formula Het-A, all of the above bases may be used, with sodium hydride (2 equivalents) giving the cleanest reaction and the highest yield of the desired product (XIII).

A wide variety of solvents may be used in Step 2 of Scheme III with the only constraint being that the solvent be inert toward starting materials (XI) and (XII) as well as to the basic reagent and the product (XIII). Suitable solvents include DMF, dimethylsulfoxide, aromatic hydrocarbons such as benzene or toluene, and ethers such as tetrahydrofuran. Step 2 may be conducted over a wide temperature range, particularly about 25° C. to 100° C. Particular conditions for effecting Step 2 of Scheme III where Het is Het-B is to use anhydrous, powdered potassium carbonate (10% excess) as the base, DMF as the solvent, and a temperature of 100° C. When Het is Het-A, particular conditions are 2.0 equivalents of sodium hydride as the base, DMF as the solvent, and a temperature of 25° C. to 50° C.

The phenols of formula (XII) employed in Step 2 of Scheme III are either known materials or may be prepared by known methods, e.g. as described by W. V. Curran et al in the Journal of Medicinal Chemistry, 17, pp 273-281 (1974); European Patent Application 178,189; or U.S. Pat. No. 4,465,686.

Step 3 in Scheme III may be effected by treating a compound of the formula (XIII) with pyridinium p-toluenesulfonate in methanol. Other methods for removing THP groups are described by T. W. Greene, *Protective Groups in Organic Synthesis*, John Wiley & sons, 1981, pp. 21-22.

An alternative route to the compounds of formula (I) in which L is (II) and $R^2$=$CH_3$ is shown in Scheme IV.

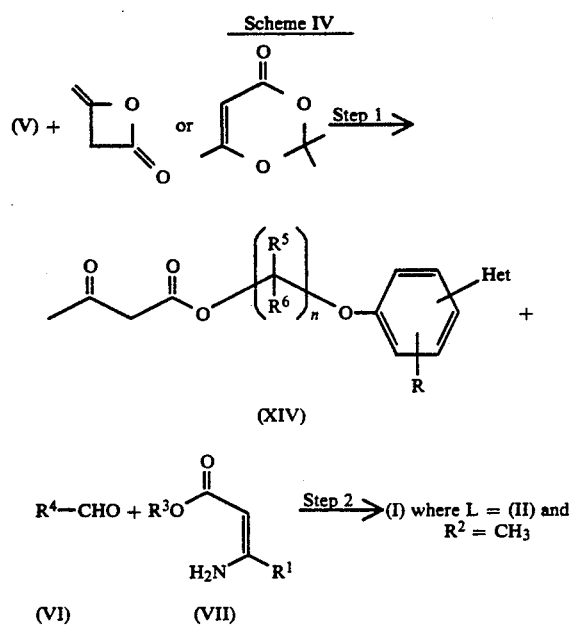

In Step 1 of Scheme IV, an alcohol of the formula (V) is converted to its corresponding acetoacetic ester of formula (XIV) by reaction with either diketene or 2,2,6-trimethyl-1,3-dioxene-4-one. If diketene is used in Step 1, the reaction is executed by heating an excess (5-25 equivalents) of diketene and the alcohol (V) in a suitable inert solvent containing a catalytic amount (about 0.1 equivalent) of an organic base. Particular conditions for effecting Step 1 with diketene are 25 equivalents of diketene, acetone as the solvent, 0.1 equivalent of triethylamine as the base, and a temperature of 50°-65° C.

If 2,2,6-trimethyl-1,3-dioxene-4-one is used, the reaction is effected by heating the alcohol (V) and 2,2,6-trimethyl-1,3-dioxene-4-one in a suitable inert solvent containing a catalytic amount of an organic acid. Preferred conditions for effecting Step 1 of Scheme IV with 2,2,6-trimethyl-1,3-dioxene-4-one are to use a 10% excess of this reagent, toluene as the solvent, p-toluenesulfonic acid as the catalyst, and a temperature in the range of 100°-125° C.

Step 2 of Scheme IV is executed as described previously for Step 1 of Scheme II with a molar ratio of (XIV):(VI):(VII) of about 1:1:1.

The compounds of formula (I) in which L=(III) may be prepared as shown in Scheme V where the R groups, y and Het are as defined for formula (I).

Scheme V

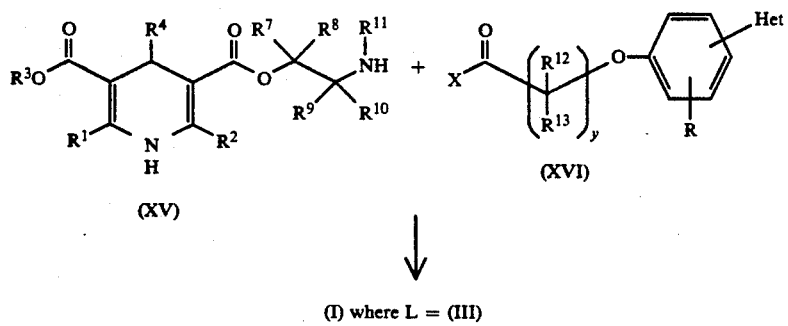

The reaction of compounds of the formula (XV) with compounds of the formula (XVI) as shown in Scheme V is executed under the same conditions described earlier for the reaction of compounds of formula (IV) with compounds of the formula (V) shown in Scheme I. In Scheme V, compounds of formulae (XV) and (XVI) are reacted in a molar ratio of about 1:1 at a temperature of about 25° to 75° C. in the presence of an inert solvent such as DMF.

In the compound of formula (XVI), X is a leaving group as defined for formula (IV), e.g. hydroxy whereby (XVI) is a carboxylic acid. Alternatively, the compound of formula (XVI) where X is hydroxy may be converted to a suitable reactive derivative which is then reacted with the amine (XV) in Scheme V. Suitable reactive derivatives of the carboxylic acid (XVI) include: acid halides, such as the acid chloride; mixed anhydrides of the carboxylic acid with another organic acid, such as acetic or propionic acid; acylimidazoles; and active esters of the carboxylic acid such as the 4-nitrophenyl ester. These active derivatives of the carboxylic acid (XVI) where X=OH may be prepared as described earlier for the acid of formula (IV) in Scheme I.

The compounds of formula (XV) in Scheme V may be synthesized as shown in Scheme VI.

Scheme VI

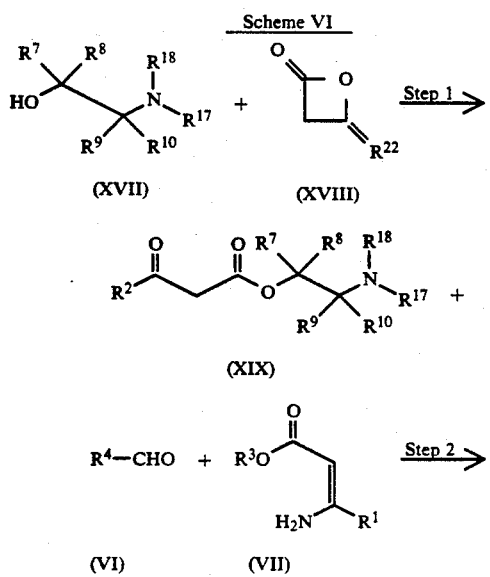

-continued
Scheme VI

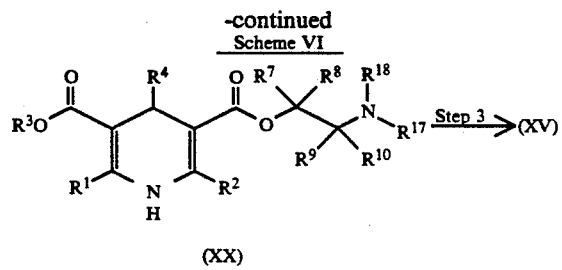

The various compounds of Scheme VI have the R definitions of formula (I). $R^{17}$ represents a monovalent amine protecting group, e.g. a tert-butoxycarbonyl group and $R^{18}$ represents lower alkyl or if $R^{11}$ in (XV) is to be hydrogen, then $R^{17}$ and $R^{18}$ together represent a divalent amine protecting group such as a phthalimide. Compounds of the formula (XVII) may be readily prepared form the corresponding commercially available $\beta$-amino alcohols by conventional methods. Compounds of the formula (XVIII) represent $\beta$-alkenyl-$\beta$-lactones that are commercially available or may be prepared by methods known in the art. In formula (XVIII), $R^{22}$ is a value of $R^2$ in formula (XIX) wherein there is one less hydrogen attached to the first carbon of the $R^2$ group. For example, $R^{22}$ can be =CH$_2$ whereby $R^2$ in (XIX) is —CH$_3$.

Step 1 in Scheme VI is executed as described for Step 1 in Scheme IV. Step 2 of Scheme VI is conducted as described for Step 1 of Scheme II. Step 3 in Scheme VI, removal of the amine protecting group, is executed under conditions appropriate to the particular amine protective group. When $R^{14}$ in Scheme VI represents the tert-butoxycarbonyl group, Step 3 is effected with an acid solution, which may be either a mineral acid such as hydrochloric acid or an organic acid such as trifuloroacetic acid. A wide range of solvents may be used for removal of the tert-butoxycarbonyl as long as the solvent is stable to acids and does not react with the amine product, (XV). Suitable solvents include the halogenated hydrocarbons such as methylene chloride or chloroform and an aromatic solvent such as benzene or toluene. The reaction may be run over a wide range of temperatures, but is generally carried out in the temperature range of 0° C. to 25° C.

In Scheme VI if $R^{17}$ and $R^{18}$ and taken together represent a phthalimide protecting group, Step 3 is conveniently executed by treatment of the compound of formula (XX) with hydrazine in a suitable solvent. Solvents that may be used for this reaction include alcohols, e.g. ethanol or isopropanol, ethers such as tetrahydrofuran, acetonitrile, or an aromatic hydrocarbon solvent such as benzene or toluene. The reaction may be executed over a wide temperature range, but the preferred temperature is 25° C. to 100° C.

The compounds of formula (XVI) in Scheme V are either known compounds as in European Pat. Appl. 178,189, may be prepared by analogous methods with substitution of starting materials or may be prepared as shown in Scheme VII.

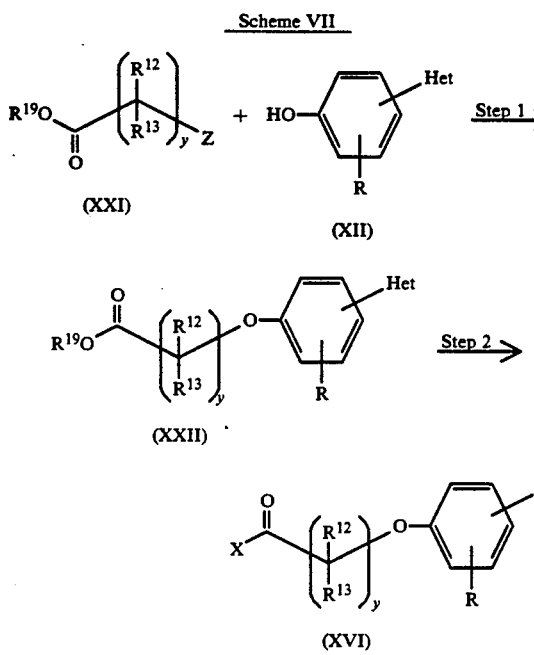

In Scheme VII, $R^{12}$, $R^{13}$, y and Het are as defined previously. In the compounds of formula (XXI), Z represents a leaving group that is reactive toward displacement by nucleophiles. Suitable Z groups include halogen, the p-toluenesulfonate ester, the p-nitrobenzenesulfonate ester, the methanesulfonate ester, and the trifluormethanesulfonate ester. $R^{19}$ in Scheme VII represents a lower alkyl group. The compounds of Scheme (VII) are known compounds or may be prepared from known compounds by conventional methods.

Step 1 in Scheme VII is executed by reacting a compound of formula (XXI) with a compound of formula (XII) in the presence of a suitable base and solvent to give compounds of the formula (XXII). The choice of base used in Step 1 of Scheme VII is dependent upon the definition of Het. If Het is of the formula Het-A, suitable bases are sodium hydride, potassium carbonate, potassium t-butoxide, and similar non-nucleophilic basic reagents. If Het is of the formula Het-B, such bases may be used, with sodium hydride (2 equivalents) giving the cleanest reaction and the highest yield of the desired product (XXII). A wide variety of solvents may be used in Step 1 of Scheme VII with the only restriction being that the solvent be inert toward starting materials (XXI) and (XII) as well as to the basic reagent and product (XXII). Suitable solvents include DMF, DMSO, an aromatic hydrocarbon such as benzene or toluene, or an ether such as THF. Step 1 in Scheme VII may be conducted over a wide temperature range, e.g. 0° C. to 80° C. Particular conditions for effecting Step 1 of Scheme VII is to use sodium hydride as the base, DMF as the solvent, and a temperature of 0° C. with gradual warming to 80° C.

Step 2 of Scheme VII is effected by heating the ester of formula (XXII) in an aqueous solution containing a base such as sodium hydroxide, potassium hydroxide and potassium carbonate. Suitable co-solvents with water for use in Step 2 include an alcohol, e.g. methanol, ethanol, or propanol; an ether, e.g. THF or dioxane; and DMSO. Step 2 may be conducted over a wide temperature range with a particular temperature being in the range of 25° C. to 80° C. The preferred conditions for effecting Step 2 of Scheme VII is to use potassium hydroxide as the base, 1:1 water:ethanol as the solvent, and a temperature of 80° C.

In formulae (XXII) and (XVI), Het may in particular be Het-A, with the resulting formulae being designated as XXII-A and XVI-A, respectively.

An alternative approach to the compounds of formula (I) in which L=(III) is shown in Scheme VIII below. The compounds of the formula (XXIII) are prepared as shown in Scheme IX. In Schemes VIII and IX, , y and Het are as defined in formula (I). Compounds of the formula (XXIV)

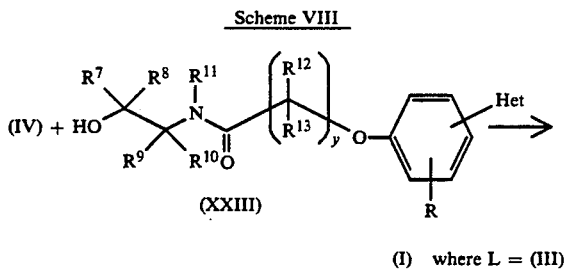

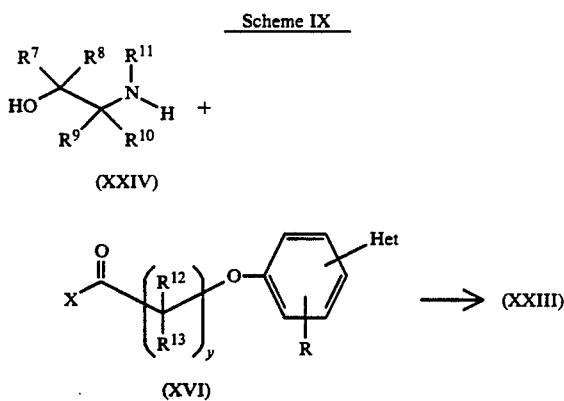

used as starting materials in Scheme IX are commercially available or may be prepared by conventional methods from known materials. The reactions illustrated in Schemes VIII and IX are executed as described earlier for the reaction of compounds of the formula (IV) with compounds of the formula (V) as shown in Scheme I. Compounds of formulae (IV) and (XXIII) are reacted in a molar ratio of about 1:1 at a temperature of about 25° to 100° C. Compounds of formulae (XXIV) and (XVI) are reacted in a molar ratio of about 1:1 at a temperature of about 25° to 75° C.

SPECIFIC COMPOUNDS

Particular compounds of formula (I) according to the present invention are those set forth in the following Table I.

TABLE I

Formula (I): $R^1, R^2, R^3, R^{14} = CH_3; R^5 - R^{13} = H; R^{15} = CN$

| Example | $R^4$ | L | n/y | Het | $R^{16}$ | R |
|---|---|---|---|---|---|---|
| 1 | 3-NO$_2\phi$ | bond | — | A/para | — | H |
| 2 | 3-NO$_2\phi$ | bond | — | A/meta | — | H |
| 3 | 3-NO$_2\phi$ | bond | — | B/para | CH$_3$ | H |
| 4 | 2-CF$_3\phi$ | bond | — | A/para | — | H |
| 5 | 2-CF$_3\phi$ | bond | — | A/meta | — | H |
| 6 | 2-CF$_3\phi$ | bond | — | B/para | CH$_3$ | H |
| 7 | 3-NO$_2\phi$ | (II) | 3 | B/para | CH$_3$ | H |
| 8 | 3-NO$_2\phi$ | (II) | 3 | A/para | — | H |
| 9 | 3-NO$_2\phi$ | (III) | 1 | B/para | CH$_3$ | H |
| 10 | 3-NO$_2\phi$ | (III) | 1 | A/para | — | H |
| 11 | 2,3-diCl$_2\phi$ | (III) | 1 | A/para | — | H |
| 12 | 3-NO$_2\phi$ | (III) | 1 | B/para | H | H |
| 13 | 2,3-diCl$_2\phi$ | (III) | 1 | B/para | CH$_3$ | H |
| 14 | 3-NO$_2\phi$ | (III) | 1 | B/para | H | Cl/ortho |
| 15* | 3-NO$_2\phi$ | (III) | 1 | A/para | — | H |
| 16* | 3-NO$_2\phi$ | (III) | 1 | A/para | — | H |
| 17 | 2-Cl-3-NO$_2\phi$ | (III) | 1 | A/para | — | H |
| 18 | 2-NO$_2\phi$ | (III) | 1 | A/para | — | H |
| 19 | 2-Cl$\phi$ | (III) | 1 | A/para | — | H |
| 20 | 3-NO$_2\phi$ | (II) | 3 | B/para | H | Cl/ortho |
| 21 | 2-NO$_2\phi$ | bond | — | B/para | CH$_3$ | H |
| 22 | 2,3-diCl$_2\phi$ | bond | — | B/para | CH$_3$ | H |
| 23 | 2-Cl$\phi$ | (III) | 1 | B/para | CH$_3$ | H |

*enantiomer

PHARMACOLOGY

The efficacy of compounds of the present invention as antihypertensive agents in view of their activity as vasodilators can be evaluated and measured using pharmacological methods known in the art or as described in detail below based on similarly established methodologies.

1. Spontaneously Hypertensive Rat (SHR) Test

Male Retired Breeder Spontaneously Hypertensive Rats (SHR) (Sprague Dawley, 250-350 g) are anesthetized by i.p. injection of Sodium Thiopental 50 mg/kg. A catheter is inserted into the duodenum for maintenance of anesthesia throughout the experiment. A tube is inserted through a lateral incision in the trachea. The left carotid artery is exposed and a Millar SPR-249 (2-F) pressure probe is inserted and passed into the left ventricle of the heart. Left ventricular pressure (LVP), the first differential of the LVP (+dP/dT,−dP/dT), the left ventricular end diastolic pressure (LVEDP) and the differential of the increase in LVP measured at a constant pressure of 40 mm Hg (dP/dT40) are measured via this probe. In addition to these parameters, two indices of myocardial diastolic relaxation are measured namely the RT64 (time in msec from the peak derivative of maximal relaxation to 64% of that value) and the Left Ventricular Pressure Time Constant (LVPT), the half-time for decay of the LVP from peak pressure to 50% of that pressure. These data are processed with a Buxco Model CH04 Hemodynamics Analyzer and recorder on line on an IBM-PC AT computer. Results also are shown graphically on a Gould RS3800 Recorder. A saline filled cannula is passed into the femoral vein for infusion of drugs and one is placed into the femoral artery for measurement and recording or arterial blood pressure (Statham P23Db pressure transducer). From this signal the diastolic, systolic and mean blood pressure are derived as well as the heart rate. After surgery, the preparation is left to stabilize for 45 minutes after which compounds, dissolved in polyethylene glycol, are slowly infused with a Sage Instruments Infusion pump into the femoral vein. Compounds either are infused cumulatively in doses of 0.3, 1.0, 3.0 and 10 mg/kg each infused over a five minute period with a five minute drug-free period between doses or in a single 5 minute infusion of one dose (3.0 or 10 mg/kg). After completion of the last infusion, hemodynamic parameters are observed over 30 min and then a standard dose of 3.0 mg/kg milrinone is infused (over 5 min) to test preparation responsiveness. In the SHR, the following results were obtained for several known cardiovascular agents and for the compound of Examples 10, 11, 15 and 16.

As set forth in Table II, in a dose range of 0.3 to 3 mg/kg (i.v.) milrinone produced hypotension, tachycardia, an increase in dP/dT40 and a decrease in myocardial relaxation time constants (increased rate of relaxation). Nifedipine (0.1 to 3 mg/kg i.v.) produced hypotension, little change in heart rate, a depression of dP/dT40 and significant reduction of myocardial relaxation time constants only at the highest dose tested (3 mg/kg). Hydralazine (0.3 to 10 mg/kg i.v.) produced hypotension, reflex tachycardia, little change in dP/dT40 and reduction in myocardial relaxation time constants only at 3 and 10 mg/kg. The compound produced in Example 10 (0.3 to 10 mg/kg i.v.) produced hypotension, little change in heart rate, an increase in dP/dT40 and reduction in the time constants for myocardial relaxation. A similar profile was observed for the product of Example 11. The product of Examples 15 and 16 produced hypotension with no change in heart rate and slight increase in dP/dT40 at 10 mg/kg i.v.; Whereas the latter produced a marked reduction in myocardial relaxation time constants, the former had little effect.

TABLE II

Hemodynamics in Anesthetized Spontaneously Hypertensive Rats

| Drug | Dose[1] mg/kg | MBP[2] | HR[3] | dP/dT40 | RT64[5] | LVPT[6] |
|---|---|---|---|---|---|---|
| Milrinone | 0.3 | −10% | 10% | 27% | −13.7% | −15.5% |
|  | 1.0 | −29% | 12.4% | 28.3% | −20.5% | −22% |
|  | 3.0 | −29% | 16.2% | 34% | −36% | −30% |
| Nifedipine | 0.1 | −12% | 3% | 7.5% | −7% | −8% |
|  | 0.3 | −30% | 1% | 2% | −7% | 3% |
|  | 1.0 | −47.5% | −5% | −15.5% | −21% | −7% |
|  | 3.0 | −47.5% | −7.5% | −28.8% | −25% | −18.5% |
| Hydral[7] | 0.3 | −1.2% | 0% | 0% | 2% | 4.1% |
|  | 1.0 | −17.8% | 8% | 3.4% | 0% | 2.3% |
|  | 3.0 | −37.5% | 8.8% | 0% | 12.5% | −7.8% |
|  | 10 | −48% | 17% | 6.9% | −22.6% | −21.9% |
| Example 10 | 0.3 | −2.6% | −1.8% | 0% | −2.6% | −5.1% |
|  | 1.0 | −3.8% | −2.5% | 1.5% | −5.2% | −7.4% |

TABLE II-continued

Hemodynamics in Anesthetized Spontaneously Hypertensive Rats

| Drug | Dose[1] mg/kg | MBP[2] | HR[3] | dP/dT40 | RT64[5] | LVPT[6] |
|---|---|---|---|---|---|---|
|  | 3.0 | −6.3% | 1.1% | 4.2% | −13.2% | −14% |
|  | 10 | −23% | 6.4% | 24.7% | −19.3% | −25% |
| Example 11 | 0.3 | −12.5% | 2.8% | 4.5% | −15.7% | −14.4% |
|  | 1.0 | −16.3% | 1.7% | 6.9% | −22.8% | −22.4% |
|  | 3.0 | −36.7% | −0.5% | 3.5% | −26% | −34% |
|  | 10 | −45.8% | 0% | −9% | −34.5% | −31% |
| Example 15 | 10 | −39.8% | −1.9% | 11.9% | 1.6% | −4.2% |
| Example 16 | 10 | −34.9% | −1.5 | −17.6% | −18% |  |

[1] i.v.
[2] Mean Blood Pressure: Change from basal measured in mm Hg
[3] Heart Rate: Change from basal measured in beats/min
[4] dP/dT40: Change in the rate of systolic pressure increase of Left Ventricle measured at 40 mm Hg from basal measured in mm Hg.
[5] RT64: Change, comparing before and after drug administration, between the time from the maximal relaxation to 65% of that rate. Expressed as % of basal.
[6] LVPT: Time (in msec) for Left Ventricular Pressure to decay from maximal peak pressure to 50% of that pressure. Expressed as % of basal.
[7] Hydral: Hydralazine

2. Rat Aorta Protocol

Rings of rat aorta (endothelium removed) were prepared for the measurement of isometric force in isolated tissue organ chambers essentially as previously described by T. J. Rimele et al in the *Journal of Pharmacol. Exp. Ther.* 245:102-111 (1988). The experimental portion of the protocol began with the addition of methylene blue ($1\times10^{-5}$M) and propranolol ($1\times10^{-6}$M) to each organ chamber to inhibit basal cGMP accumulation due to soluble guanylate cyclase and beta-adrenoceptors. Phenylephrine ($1\times10^{-7}$M) was then added and the rings were allowed to obtain a stable contractile response after which time, the test compound was added in a cumulative fashion. The relaxation induced by each concentration of the test compound was expressed as a percentage of the maximal relaxation produced by nitroprusside ($1\times10^{-4}$M). The results were graphically represented as a plot of the percentage relaxation vs. the negative log of the molar concentration of the test compound. The $IC_{50}$ (concentration of test compound which produced a relaxation equivalent to 50% of the maximal relaxation induced by nitroprusside) was determined for each tissue. The $IC_{50}$ for the compound of Example 10 was $2.1\times10^{-6}$ molar with the maximal response being 96% at the highest dose tested (100 micromolar).

Pharmaceutical Formulation and Doses

Compounds of the invention of formula (I) may be used in the treatment of hypertension in a manner similar to the use of nifedipine.

The compounds of the invention of formula (I) can be administered orally, topically or parenterally, e.g. rectal or i.v., of which the preferred route is oral. The compounds may be admixed with conventional tableting aids, diluents, excepients as known in the art to form tablets, capsules, powders, elixirs, liquids or suspensions as known in the pharmaceutical art. For administration to humans, the compounds of the invention may be administered in an amount of about 0.1 to 1 mg/kg, in particular about 0.2 to 0.4 mg/kg about 2 to 4 times per day. The particular dosage will depend on the activity of the specific compound chosen and the severity of the physiological condition being treated. The projected dosage can be determined by correlation of test results in pharmacological tests for known vasodialtion agents such as nifedipine to those for compounds of formula (I).

In the following examples and throughout the specification, the following abbreviation may be used: g (grams),; mg (milligrams); mg/kg (milligrams per kilogram of body weight); l (liters); ml (milliliters); M (molar); mM (millimolar); i.v. (intraveneous); Hz (Hertz); dP/dt (change in pressure per time period); mol (moles); DMF (N,N-dimethylformamide); THP (tetrahydropyran); DMSO (dimethylsulfoxide); TFA (trifluoroacetic acid); THF (tetrahydrofuran); DCC (dicyclohexylcarbodiimide): NMR (nuclear magnetic resonance); t (triplet); m (multiplet); s (singlet); d (doublet); RT (room temperature); EtOAc (ethyl acetate); min (minutes); hr (hours); m.p. (melting point); $\phi$ (monovalent phenyl group); and TLC (thin layer chromatography).

Unless otherwise indicated, all temperatures are expressed in °C. (degrees Centigrade), pressures in mmHg (millimeters of mercury) and all references to ether are to diethyl ether.

EXAMPLE 1

(±)-2,6-dimethyl-3-carbomethoxy-4-(3-nitrophenyl)-5-{4-[1,2-dihydro-2-oxo-3-cyano-6-methyl-5(1H)-pyridyl]phenoxycarbonyl}-1,4-dihydropyridine A solution of 290 mg (0.873 mmol) of (±)-2,6-dimethyl-3-carbomethoxy-4-(3-nitrophenyl)-5-carboxy-1,4-dihydropyridine prepared using the methods described in Ger. Offen DE 2847236, 183 mg (0.873 mmol) of 5-(4-hydroxyphenyl)-6-methyl-2-oxo-1,2-dihydro-3-pyridinecarbonitrile prepared as described in U.S. Pat. No. 4,465,686 and 198 mg (0.960 mmol) of DCC in 7.0 ml of DMF containing 11.0 mg (0.087 mmol) of 4-dimethylaminopyridine is heated at 80° C. under a $N_2$ atmosphere for 24 hr.

After cooling, the precipitate of dicyclohexylurea is removed by filtration, washed with a few ml of THF, and the combined filtrate poured into 150 ml of ice water. After stirring for 10-15 min the precipitate is collected by filtration, the precipitate taken up in about 200 ml of THF, dried (MgSO$_4$), filtered, and the solvent removed under vacuum to leave a light brown solid. This solid is triturated with EtOAc followed by methylene chloride and the resulting solid dried under vacuum to give 185 mg of the title compound as a light yellow solid, m.p. 253°-255° C. Elemental Anaylsis (for $C_{29}H_{24}N_4O_7$)

| Elemental Analysis (for C₂₉H₂₄N₄O₇) | | | |
|---|---|---|---|
| | % C | % H | % N |
| Found: | 64.36 | 4.50 | 10.27 |
| Calculated: | 64.44 | 4.48 | 10.37 |

EXAMPLE 2

(±)-2,6-dimethyl-3-carbomethoxy-4-(3-nitrophenyl)-5-{3-[1,2-dihydro-2-oxo-3-cyano-6-methyl-5(1H)-pyridyl]phenoxycarbonyl}-1,4-dihydropyridine A solution of 250 mg (0.752 mmol) of (±)-2,6-dimethyl-3-carbomethoxy-4-(3-nitrophenyl)-5-carboxy-1,4-dihydropyridine, 158 mg (0.752 mmol) of 5-(3-hydroxyphenyl)-6-methyl-2-oxo-1,2-dihydro-3-pyridinecarbonitrile, 171 mg (0.827 mmol) of DCC and 9 mg (0.075 mmol) of 4-dimethylaminopyridine in 3.5 ml of DMF is heated at 80° C. for 18 hr under N₂. After cooling, the dicyclohexylurea was removed by filtration and washed with EtOAc. The combined filtrate is diluted with 45 ml of EtOAc, washed with water (3×20 ml), dried (MgSO₄), filtered, and the solvent removed under vacuum to leave a dark yellow residue. This residue is flash chromatographed on silica gel (4:1 EtOAc:hexane), and the resulting product recrystallized from hexane:EtOAc to give 200 mg of the title compound as a yellow solid, m.p. 209°–211° C.

| Elemental Analysis (for C₂₉H₂₄N₄O₇·½ H₂O) | | | |
|---|---|---|---|
| | % C | % H | % N |
| Found: | 63.58 | 4.53 | 10.11 |
| Calculated: | 63.38 | 4.59 | 10.20 |

EXAMPLE 3

(±)-2,6-dimethyl-3-carbomethoxy-4-(3-nitrophenyl)-5-{4-[2,3,4,5-tetrahydro-3-oxo-5-methyl-6(2H)-pyridazinyl]phenoxycarbonyl}-1,4-dihydropyridine A solution of 250 mg (0.752 mmol) of (±)-2,6-dimethyl-3-carbomethoxy-4-(3-nitrophenyl)-5-carboxy-1,4-dihydropyridine, 153 mg (0.752 mmol) of 6 (4-hydroxyphenyl)-5-methyl-4,5-dihydro-3(2H)-pyridazinone prepared as described in Eur. Pat. Appl. 178,189, 171 mg (0.827 mmol) of DCC, and 9 mg (0.075 mmol) of 4-dimethylaminopyridine in 3 ml of DMF is heated at 80° C. for 16 hr under N₂. After cooling, the precipitate of dicyclohexyl urea is removed by filtration, washed with EtOAc, and the combined filtrate diluted with about 40 ml of EtOAc. The organic phase is washed with water (3×25 ml), dried (MgSO₄), filtered, and the solvent removed under vacuum to give a yellow residue. This residue is flash chromatographed on silica gel (2:1 CHCl₃:EtOAc) to give a yellow oil. This oil is crystallized from hexane-EtOAc to give 304 mg of the title compound as a yellow solid, m.p. 199°–201° C.

| Elemental Analysis (for C₂₇H₂₆N₄O₇·½ H₂O): | | | |
|---|---|---|---|
| | % C | % H | % N |
| Found: | 61.91 | 5.40 | 9.91 |
| Calculated: | 61.45 | 5.16 | 10.62 |

EXAMPLE 4

(±)-2,6-dimethyl-3-carbomethoxy-4-(2-trifluoromethylphenyl) 5-{4-[1,2-dihydro-2-oxo-3-cyano-6-methyl-5(1H)-pyridyl]phenoxycarbonyl}-1,4-dihydropyridine A solution of 250 mg (0.704 mmol) of (±)-2,6-dimethyl-3-carbomethoxy-4-(2-trifluoromethylphenyl)-5-carboxy-1,4-dihydropyridine prepared as described in Ger. Offen DE 3209276, 148 mg (0.704 mmol) of 5-(4-hydroxyphenyl)-6-methyl-2-oxo-1,2-dihydro-3-pyridinecarbonitrile, 160 mg (0.774 mmol) of DCC, and 8 mg (0.07 mmol) of 4-dimethylaminopyridine in 3.5 ml of DMF is heated at 80° C. for 20 hr. After cooling, the dicyclohexylurea is collected by filtration, washed with EtOAc, and the filtrate diluted with 150 ml of EtOAc. The organic phase is washed with water (3×50 ml), dried (MgSO₄), and the solvent removed under vacuum. The residue is flash chromatographed on silica gel (95:5 CHCl₃:CH₃OH) to give 326 mg of the title compound as a pale yellow solid, m.p. 250°–252° C.

| Elemental Analysis (for C₃₀H₂₄F₃N₃O₅): | | | |
|---|---|---|---|
| | % C | % H | % N |
| Found: | 63.92 | 4.29 | 7.40 |
| Calculated: | 63.94 | 4.29 | 7.46 |

EXAMPLE 5

(±)-2,6-dimethyl-3-carbomethoxy-4-(2-trifluoromethylphenyl)-5-{3-[1,2-dihydro-2-oxo-3-cyano-6-methyl-5(1H)-pyridyl]phenoxycarbonyl}-1,4-dihydropyridine A solution of 244 mg (0.687 mmol) of (±)-2,6-dimethyl-3-carbomethoxy-4 (2-trifluoromethylphenyl)-5-carboxy-1,4-dihydropyridine, 144 mg (0.687 mmol) of 5-(3-hydroxyphenyl)-6-methyl-2-oxo-1,2-dihydro-3-pyridinecarbonitrile, 156 mg (0.755 mmol) of DCC, and 8 mg (0.069 mmol) of 4-dimethylaminopyridine in 3 ml of DMF is heated at 80° C. for 18 hr under N₂. After cooling, the dicyclohexylurea is removed by filtration and washed with EtOAc. The filtrate is diluted with 50 ml of EtOAc, washed with H₂O (3×25 ml), dried (MgSO₄), and the solvent removed under vacuum. The residue is flash chromatographed on silica gel (4:1 EtOAc:hexane) and the resulting product is crystallized from EtOAc to give 245 mg of the title compound as a pale yellow solid, m.p. >275° C.

| Elemental Analysis (for C₃₀H₂₄F₃N₃O₅) | | | |
|---|---|---|---|
| | % C | % H | % N |
| Found: | 62.31 | 4.46 | 7.20 |
| Calculated: | 61.96 | 4.51 | 7.23 |

EXAMPLE 6

(±)-2,6-dimethyl-3-carbomethoxy-4-(2-trifluoromethylphenyl)-5-{4-[2,3,4,5-tetrahydro-3-oxo-5-methyl-6(2H)-pyridazinyl]phenoxycarbonyl}-1,4-dihydropyridine A solution of 252 mg (0.709 mmol) of (±)-2,6-dimethyl-3-carbomethoxy-4-(2-tifuloromethylphenyl)-5-carboxy 1,4-dihydropyridine, 144 mg (0.709 mmol) of 6-(4-hydroxyphenyl)-5-methyl-4,5-dihydro-3(2H)-pyridazinone, 161 mg of DCC, and 9 mg (0.071 mmol) of 4- dimethylaminopyridine in 3 ml of DMF is heated at 80° C. for 16 hr. After cooling, the dicyclohexylurea is collected by filtration and washed with EtOAc. The filtrate is diluted with 50 ml of EtOAc, washed with water (3×25 ml), dried (MgSO₄), and the solvent removed under vacuum. The residue is flash chromatographed on silica gel (97:3 CHCl₃:CH₃OH) and the product recrystallized from EtOAc:ether to give 118 mg of the title compound as a pale yellow solid, m.p. 228°-230 C.

| Elemental Analysis (for $C_{28}H_{26}F_3N_3O_5$) | | | |
|---|---|---|---|
| | % C | % H | % N |
| Found: | 62.27 | 4.97 | 7.64 |
| Calculated: | 62.10 | 4.84 | 7.76 |

EXAMPLE 7

(±)-2,6-dimethyl-3-carbomethoxy-4-(3-nitrophenyl)-5-{4-[2,3,4,5-tetrahydro-3-oxo-5-methyl-6(2H)-pyridazinyl]phenoxypropyloxycarbonyl}-1,4-dihydropyridine A solution of 7.50 ml (82.9 mmol) of 3-bromo-1-propanol and 1.38 g (5.5 mmol) of pyridinium p-toluenesulfonate in 20 ml of CH₂Cl₂ is stirred under N₂ while cooled in an ice water bath. To this solution is added, dropwise, 11.4 ml (124.4 mmol) of 3,4-dihydro-2H-pyran, and the reaction is allowed to warm slowly to RT and stirred overnight under N₂. The reaction mixture is washed with 50% NaCl solution, dried (MgSO₄), and subjected to fractional vacuum distillation. The desired THPyl ether of 3-bromo-1-propanol is collected at 113°-118° C./50 mm. Yield: 4.52 g ¹H-NMR (CDCl₃): δ 1.50 (m, 4H); 1.70 (m, 2H); 2.10 (quintuplet, 2H); 3.48 (t pair, 4H); 3.80 (m, 2H); 4.57 (m, 1H).

A solution of 361 mg (1.62 mmol) of the THP-derivative of 3-bromo-1-propanol prepared above, 220 mg (1.08 mmol) of 6-(4-hydroxyphenyl)-5-methyl-4,5-dihydro-3(2H)-pyridazinone and 298 mg (2.15 mmol) of powdered anhydrous potassium carbonate in 3 ml of DMF is heated at 100° C. for 2 hr. After cooling the reaction mixture is diluted with 25 ml of water and extracted with EtOAc (3×25 ml). The combined organic extracts are washed once with water, dried (MgSO₄), filtered, and the solvent removed under vacuum. The residue is taken up in 5 ml of methanol, about 200 mg of pyridinium p-toluenesulfonate added, and the mixture heated at 60° C. for 2 hr under N₂. The solvent is removed under vacuum and the residue is flash chromatographed on silica gel (95:5 CHCl₃:CH₃OH) to give 252 mg of 6-[4-(3-hydroxypropyloxy)phenyl]-5-methyl-4,5-dihydro-3(2H)-pyridazinone as a white solid. ¹H-NMR (CDCl): δ1.18 (d, 3H); 1.83 (t, 1H); 2.00 (quintuplet, 2H); 2.40 (d, 1H); 2.63 (d pair, 1H); 3.25 (m, 1H); 3.80 (m, 2H); 4.10 (t, 2H); 6.90 (d, 2H); 7.63 (d, 2H); 8.65 (s, 1H).

A solution of 250 mg (0.752 mmol) of (±)-2,6-dimethyl-3-carbomethoxy-4-(3-nitrophenyl)-5-carboxy-1,4-dihydropyridine, 196 mg (0.752 mmol) of 6-[4-(3-hydroxypropyloxy)]phenyl]-5-methyl-4,5-dihydro-3(2H)pyridazinone, 171 mg (0.827 mmol) of DCC, and 9 mg (0.075 mmol) of 4-dimethylaminopyridine in 3 ml of DMF is heated overnight at 80° C. under N₂. After cooling, the dicyclohexylurea is removed by filtration, the urea washed with EtOAc, and the combined filtrate diluted with 50 ml of EtOAc. The organic phase is washed with water (3×25 ml), dried (MgSO₄), filtered, and the solvent removed under vacuum. The residue is flash chromatographed on silica gel (95:5 CHCl₃:CH₃OH) to give 253 mg of the title compound as a yellow solid, m.p. 92°-100° C.

| Elemental Analysis (for $C_{30}H_{32}O_8 \cdot \tfrac{1}{4} H_2O$) | | | |
|---|---|---|---|
| | % C | % H | % N |
| Found: | 61.73 | 5.80 | 9.13 |
| Calculated: | 61.64 | 5.52 | 9.58 |

EXAMPLE 8

(±)-2,6-dimethyl-3-carbomethoxy-4-(3-nitrophenyl)-5-{4-[1,2-dihydro-2-oxo-3-cyano-6-methyl-5(1H)-pyridyl]phenoxypropyloxycarbonyl}-1,4-dihydropyridine A clean and dry round-bottom flask is charged with 144 mg (5.99 mmol) of 60% NaH dispersion in mineral oil. The oil is removed by washing the NaH with hexane (2×5 ml) A solution of 378 mg (1.80 mmol) of 5-(4-hydroxyphenyl)-6-methyl-2-oxo-1,2-dihydro-3-pyridinecarbonitrile in 5 ml of DMF is added to the NaH. The mixture is stirred 30 min at RT at which time a clear solution results. A solution of 602 mg (2.70 mmol) of the tetrahydropyranyl ether of 3-bromo-1-propanol (prepared as described in Example 7) is added all at once to the reaction mixture, and the solution is heated at 50° C. under N₂ for 1 hr. The reaction is allowed to cool, diluted with 25 ml of water, and extracted with EtOAc (3×25 ml). The combined EtOAc extracts are washed with water, dried (MgSO₄), filtered, and the solvent removed under vacuum. The residue is taken up in 7 ml of methanol, about 300 mg of pyridinium p-toluenesulfonate added, and the mixture heated at reflux under N₂ for 6 hr. The solvent is then removed under vacuum and the residue is flash chromatographed on silica gel (95:5 CHCl₃:CH₃OH) to give 209 mg of 5-[4-(3-hydroxypropyloxy)phenyl]-6-methyl-2-oxo-1,2-dihydro3-pyridinecarbonitrile as a white solid. ¹H-NMR (d₆-DMSO): δ 1.85 (quintuplet, 2H); 2.22 (s, 3H); 3.55 (m, 2H); 4.08 (t, 2H); 4.58 (t, 1H); 6.95 (d, 2H); 7.25 (d, 2H); 8.02 (s, 1H).

A solution of 360 mg (1.08 mmol) of (±)-2,6-dimethyl-3-carbomethoxy-4-(3-nitrophenyl)-5-carboxy-1,4-dihydropyridine, 289 mg (1.08 mmol) of 5-[4 (3-hydroxypropyloxy)phenyl-6-methyl-2-oxo-1,2-dihydro-3-pyridinecarbonitrile, 267 mg (1.29 mmol) of DCC, and 26 mg (0.22 mmol) of 4-dimethylaminopyridine in 6 ml of DMF is heated for 12 hr at 90° C. After cooling, the dicyclohexylurea is removed by filtration and washed with EtOAc. The filtrate is diluted with 75 ml of EtOAc, washed with water (3×25 ml), dried (MgSO₄), filtered, and the solvent removed under vacuum. The residue is chromatographed on a chromatotron using a 4 mm silica gel plate and eluting with EtOAc. The resulting product is crystallized from methanol to give 295 mg of the title compound as a yellow solid, m.p. 251°-253° C.

| Elemental Analysis (for $C_{32}H_{30}N_4O_8$): | | | |
|---|---|---|---|
| | % C | % H | % N |
| Found: | 63.95 | 5.09 | 9.24 |
| Calculated: | 64.21 | 5.05 | 9.36 |

EXAMPLE 9

(±)-2,6-dimethyl-3-carbomethoxy-4-(3-nitrophenyl)-5-{4-[2,3,4,5-tetrahydro-3-oxo-5-methyl-6(2H)-pyridazinyl]phenoxymethylenecarboxamidoethyloxycarbonyl}-1,4-dihydropyridine A solution of 10.0 g (52.3 mmol) of N-(2-hydroxyethyl)phthalimide, 8.84 ml (67.7 mmol) of 2,2,6-trimethyl-1,3-dioxen-4-one, and 10 mg of p toluenesulfonic acid in 50 ml of toluene is heated at reflux under $N_2$ for 4 hr. The solvent is removed under vacuum and the dark-colored residue is flash chromatographed on silica gel (1:1 hexane-EtOAc). The resulting product is recrystallized from EtOAc to give 11.0 g of 2-phthalimidoethyl acetoacetate.

A solution of 5.00 g (18.2 mmol) of 2-phthalimidoethyl acetoacetate, 2.74 g (18.2 mmol) of 3-nitrobenzaldehyde, 80 μl (0.91 mmol) of piperidine, and 10 μl of acetic acid in 70 ml of benzene is heated at reflux with azeotropic removal of water for 24 hr. The solvent is then removed under vacuum to leave a dark orange residue. The residue is chromatographed on silica gel (1:1 hexane-EtOAc) to give 2.50 g of 2-phthalimidoethyl-3-nitrobenzylidene acetoacetate as a yellow solid.

A solution of 750 mg (1.84 mmol) of the 2-phthalimidoethyl 3-nitrobenzylidene acetoacetate prepared above, 211 mg (1.84 mmol) of methyl 3-aminocrotonate, and 30 ml of isopropanol is heated at reflux under $N_2$ for 18 hr. The solvent is then removed and the residue product recrystallized from EtOAc-hexane to give 681 mg of (±)-2,6-dimethyl-3-carbomethoxy-4-(3-nitrophenyl)-5-(2-phthalimidoethyloxycarbonyl)-1,4-dihydropyridine as a pale yellow solid. $^1$H-NMR ($CDCl_3$): δ 2.30 (s, 6H); 3.58 (s, 3H); 3.90 (m, 2H); 4.23 (m, 2H); 4.95 (s, 1H); 5.70 (s, 1H); 7.17 (m, 1H); 7.55 (d, 1H); 7.68 (m, 2H); 7.73 (m, 1H); 7.81 (d, 1H); 8.00 (s, 1H).

A solution of 2.32 g (4.59 mmol) of (±)-2,6-dimethyl-3-carbomethoxy-4-(3-nitrophenyl)-5-(2-phthalimidoethyloxycarbonyl)-1,4-dihydropyridine and 344 mg of hydrazine monohydrate in 100 ml of ethanol is heated at reflux for 2 hr. TLC indicates the reaction is incomplete so another 1.5 equivalents of hydrazine monhydrate is added and the mixture refluxed for an additional hr. After cooling, the precipitate is collected by filtration, washed with ethanol, and the filtrate evaporated under vacuum to leave a yellow solid. This solid is taken up in 125 ml of $CH_2Cl_2$, washed twice with 0.5N KOH, once with water, dried ($MgSO_4$), filtered, and the solvent removed under vacuum to give 1.70 g of (±)-2,6-dimethyl-3-carbomethoxy-4-(3-nitrophenyl)-5-(2-aminoethoxycarbonyl)-1,4-dihydropyridine as a yellow solid. $^1$H-NMR ($CDCl_3$); δ 1.85 (s, 2H); 2.40 (d, 6H); 3.40 (t, 2H); 3.68 (s, 3H); 4.35 (s, 2H); 5.15 (s, 1H); 5.90 (s, 1H); 7.40 (t, 1H) 7.68 (d, 1H); 8.03 (d, 1H); 8.13 (s, 1H).

A solution of 288 mg (0.767 mmol) of (±)-2,6-dimethyl-3-carbomethoxy-4-(3-nitrophenyl)-5-(2-aminoethoxycarbonyl)-1,4-dihydropyridine, 189 mg (0.767 mmol) of 6-(4-carboxymethoxyphenyl)-5-methyl-4,5-dihydro-3(2H)-pyridazinone prepared as described in Eur. Pat. Appl. 178,189 and 140 μl (0.921 mmol) of diethyl cyanophosphonate in 3 ml of DMF is cooled in an ice-water bath. To the mixture is added 210 μl (1.54 mmol) of triethylamine. The reaction mixture is allowed to slowly warm to RT and stirred overnight under $N_2$. The mixture is then diluted with 150 ml of EtOAc, the organic phase washed with 150 ml of EtOAc, the organic phase washed with 100 ml of 5% HCl, 100 ml of 25% aqueous $NaHCO_3$, and 100 ml of 25% aqueous NaCl. The EtOAc solution is dried ($MgSO_4$), filtered, and the solvent removed under vacuum to leave an orange colored residue. The residue is purified on a 2 mm thick silica gel using a chromatotron (2:1 hexane-EtOAc) to give 213 mg of the title compound as a yellow solid, m.p. 115°–120° C.

| Elemental Analysis (for $C_{31}H_{33}N_5O_9 \cdot H_2O$): | | | |
|---|---|---|---|
|  | % C | % H | % N |
| Found: | 58.77 | 5.40 | 10.83 |
| Calculated: | 58.38 | 5.22 | 10.98 |

EXAMPLE 10

(±)-2,6-dimethyl-3-carbomethoxy-4-(3-nitrophenyl)-5-{4-[1,2-dihydro-2-oxo-3-cyano-6-methyl-5(1H)-pyridyl]phenoxymethylenecarboxyamidoethyloxycarbonyl}-1,4-dihydropyridine A dispersion of 177 mg (4.4 mmol) of 60% sodium hydride in mineral oil and 15 ml of DMF is treated, in portions, with 500 mg (2.2 mmol) of 5-(4-hydroxyphenyl)-6-methyl-2-oxo-1,2-dihydro-3-pyridinecarbonitrile. After the evolution of hydrogen ceases, the reaction is stirred 30 min at RT, cooled in an ice bath, and a solution of 440 mg (2.7 mmol) of ethyl bromoacetate in 1 ml of DMF added dropwise. The reaction is stirred 30 min at 0° C., then 30 min at RT and finally heated to 80° C. for 45 min. At this time TLC (95:5 $CHCl_3:CH_3OH$) indicated none of the starting phenol is present.

The mixture is concentrated under vacuum and the residue taken up in 150 ml of EtOAc. The EtOAc is washed with water (2×75 ml) and the combined water washes acidified with 1N HCl and extracted with EtOAc (3×75 ml). The combined EtOAc extracts are dried ($MgSO_4$), the solvent removed under vacuum, and the residue flash chromatographed on silica gel (98:2 $CHCl_3:CH_3OH$) to give 290 mg of 5-(4-carboethoxymethoxyphenyl)-6-methyl-2-oxo-1,2-dihydro-3-pyridinecarbonitrile as a white solid. $^1$H-NMR ($CDCl_3$) δ 1.35 (t, 3H); 2.50 (s, 3H); 4.35 (q, 2H); 4.70 (s, 2H); 7.00 (d, 2H); 7.20 (d, 2H); 7.85 (s, 1H).

A solution of 280 mg (0.90 mmol) of the ethyl ester prepared above in 10 ml of 1:1 ethanol:water containing 151 mg (2.7 mmol) of potassium hydroxide is heated with stirring under $N_2$ at 80° C. for 2 hr. The reaction is diluted with 3× its volume of water and extracted with ether (2×50 ml). The aqueous phase is cooled in ice and acidified with 6N HCl. The resulting precipitate is collected by filtration, washed with water, and dried at 80° C. under vacuum overnight to give 250 mg of 5-(4-carboxymethoxyphenyl)-6-methyl-2-oxo-1,2-dihydro-3-pyridinecarbonitrile as a white solid. $^1$H-NMR ($d_6$-DMSO): δ 2.23 (s, 3H); 4.70 (s, 2H); 6.97 (d, 2H); 7.25 (d, 2H); 8.05 (s, 1H).

A solution of 409 mg (1.09 mmol) of (±)-2,6-dimethyl-3-carbomethoxy-4-(3-nitrophenyl)-5-(2-aminoethoxycarbonyl)-1,4-dihydropyridine (prepared as described in Example 9), 310 mg (1.09 mmol) of 5-(4-carboxymethoxyphenyl)-6-methyl-2-oxo-1,2-dihydro-3-pyridinecarbonitrile, and 200 μl (1.31 mmol) of diethyl cyanophosphonate in 5 ml of DMF is cooled in an ice-water bath and 300 μl (2.18 mmol) of triethylamine added. The mixture is allowed to slowly warm to RT and stirred overnight under $N_2$. The mixture is then diluted with 150 ml of EtOAc, washed with 5% HCl, then 25% NaHCO$_3$; and finally with 25% aqueous NaCl. The EtOAc solution is dried (MgSO$_4$), filtered, and the solvent removed under vacuum to leave an orange oil. This oil is purified on a 4 mm silica gel plate using a chromatotron and eluting with 100% EtOAc to 100% methanol. The recovered crude product is recrystallized from methanol to give 200 mg of the title compound as a yellow solid, m.p. 191°–195° C.

| Elemental Analysis (for C$_{33}$H$_{31}$N$_5$O$_9$.¼ H$_2$O): | | | |
|---|---|---|---|
| | % C | % H | % N |
| Found: | 60.56 | 4.86 | 10.82 |
| Calculated: | 60.91 | 4.96 | 10.76 |

EXAMPLE 11

(±)-2,6-dimethyl-3-carbomethoxy-4-(2,3-dichlorophenyl)-5-{4-[1,2-dihydro-2-oxo-3-cyano-6-methyl-5(1H)-pyridyl]phenoxymethylenecarboxamindoethyloxycarbonyl}-1,4-dihydropyridine A solution of 267 mg (0.675 mmol) of (±)-2,6-dimethyl-3-carbomethoxy-4-(2,3-dichlorophenyl)-5-(2-aminoethoxycarbonyl)-1,4-dihydropyridine prepared as described in Ger. Offen. DE 3,621,104, 192 mg (0.675 mmol) of 5-(4-carboxymethoxyphenyl)-6-methyl-2-oxo-1,2-dihydro-3-pyridinecarbonitrile, and 120 µl (0.810 mmol) of diethylcyanophosphonate in 3 ml of DMF is cooled in an ice bath and 190 µl (1.35 mmol) of triethylamine added. The mixture was slowly allowed to warm to RT and stirred overnight under N$_2$. The reaction mixture is then diluted with water (about 50 ml) and stirred for 30 min. A yellow precipitate which formed is collected by filtration, washed with water, and recrystallized from EtOAc to give 181 mg of the title compound as a yellow solid, m.p. 239°–242° C.

| Elemental Analysis (for C$_{33}$H$_{30}$Cl$_2$N$_4$O$_7$.H$_2$O): | | | |
|---|---|---|---|
| | % C | % H | % N |
| Found: | 57.73 | 4.60 | 8.14 |
| Calculated: | 57.98 | 4.72 | 8.20 |

EXAMPLE 12

(±)-2,6-dimethyl-3-carbomethoxy-4-(3-nitrophenyl)-5-{4-[2,3,4,5-tetrahydro-3-oxo-6(2H)-pyridazinyl]phenoxymethylenecarboxamidoethyloxycarbonyl}-1,4-dihydropyridine A solution of 250 mg (1.01 mmol) of (±)-2,6-dimethyl-3-carbomethoxy-4-(3-nitrophenyl)-5-(2-aminoethoxycarbonyl)-1,4-dihydropyridine, 378 mg (1.01 mmol) of 6-(4-carboxymethoxyphenyl)-4,5-dihydro-3(2H)-pyridazinone prepared as described in Eur. Pat. Appl. 178,189 and 180 µl (1.21 mmol) of diethycyanophosphonate in 3.5 ml of DMF is cooled in an ice-water bath, and 280 µl (2.01 mmol) of triethylamine is added. The reaction is allowed to slowly warm to RT and stirred overnight under N$_2$.

The reaction mixture is diluted with about 50 ml of H$_2$O and extracted with EtOAc (2×50 ml). The organic phase is washed with 5% HCl, then water 25% aqueous NaHCO$_3$, and again with water. The solution is dried (MgSO$_4$) and the solvent removed under vacuum to leave a yellow oil. This oil is purified on a 4 mm thick silica gel plate using a chromatotron. The crude product is recrystallized from EtOAc to give 384 mg of the title compound as a yellow solid, m.p. 211°–212° C.

| Elemental Analysis (for C$_{30}$H$_{31}$N$_5$O$_9$.¼ H$_2$O): | | | |
|---|---|---|---|
| | % C | % H | % N |
| Found: | 59.01 | 5.34 | 11.23 |
| Calculated: | 58.62 | 5.25 | 11.40 |

EXAMPLE 13

(±)-2,6-dimethyl-3-carbomethoxy-4-(2,3-dichlorophenyl)-5-{4-[2,3,4,5-tetrahydro-3-oxo-5-methyl-6(2H)-pyridazinyl]phenoxymethylenecarboxamidoethoxycarbonyl}-1,4-dihydropyridine A solution of 337 mg (0.845 mmol) of (±)-2,6-dimethyl-3-carbomethoxy-4-(2,3-dichlorophenyl)-5-(2-aminoethoxycarbonyl)-1,4-dihydropyridine, 208 mg (0.845 mmol) of 6-(4-carboxymethoxyphenyl)-5-methyl-4,5-dihydro-3(2H)-pyridazinone, and 150 µl (1.01 mmol) of diethylcyanophosphonate in 4 ml of DMF is cooled in an ice-water bath and 230 µl of triethylamine is added. The mixture is allowed to slowly warm to RT and stirred overnight under N$_2$.

The reaction mixture is diluted with about 50 ml of water and stirred for 30 min. The resulting precipitate is collected by filtration then purified on silica gel using a chromatotraon (98:2 CHCl$_3$:CH$_3$OH followed by 95:5 CHCl$_3$:CH$_3$OH) to give 229 mg of the title compound as a pale yellow solid, m.p. 184°–186° C.

| Elemental Analysis (for C$_{31}$H$_{32}$Cl$_2$N$_4$O$_7$.1¼ H$_2$O): | | | |
|---|---|---|---|
| | % C | % H | % N |
| Found: | 55.39 | 4.96 | 8.05 |
| Calculated: | 55.53 | 5.26 | 8.36 |

EXAMPLE 46

(±)-2,6-dimethyl-3-carbomethoxy-4-(3-nitrophenyl)-5-{4-[2,3,4,5-tetrahydro-3-oxo-6(2H)-pyridazinyl]-2-chloroohenoxymethylenecarboxamidoethoxcarbonyl}-1,4-dihydropyridine The procedure of Example 12 was repeated using 6-[3-chloro-4-(carboxymethoxy)phenyl]-4,5-dihydro-3(2H)-pyridazinone prepared as described in Eur. Pat. App. 178,189 in the place of 6-(4-carboxymethoxyphenyl)-4,5-dihydro-3(2H)-pyridazinone. The title product was obtained, m.p. 220°–222° C.

| Elemental Analysis for C$_{30}$H$_{30}$ClN$_5$O$_9$: | | | |
|---|---|---|---|
| | % C | % H | % N |
| Found: | 55.88 | 4.72 | 10.68 |
| Calculated: | 56.29 | 4.72 | 10.94 |

EXAMPLE 15

(+)-2,6-dimethyl-3-carbomethoxy-4-(3-nitrophenyl)-5-{4-[1,2-dihydro-2-oxo-3-cyano-6-methyl-5(1H)-pyridyl]phenoxymethylenecarboxamidoethyloxvcarbonyl}-1,4-dihydropyridine The procedure of Example 10 was carried out with the following exceptions. The carboxylic acid of formula (IV) where R$^1$=R$^2$=R$^3$=CH$_3$, R$^4$=3-nitrophenyl and X=OH as a single enantiomer, prepared as described in Eur. Pat. Appln. 249,245 was converted to the acid chloride, reacted in the presence of 4-dimethylaminopyridine as a proton acceptor with phthalimidoethanol to yield the phthalimidoethyl ester. The phthalimido group was then cleaved off with hydrazine and the product was then reacted as in Example 10 to yield the title product, m.p. 151°–153° C., $[\alpha]_D^{23} = +19.6°$ C. (C=0.51, acetone).

| Elemental Analysis for $(C_{33}H_{31}N_5O_9 \cdot \frac{1}{2} H_2O)$: | | | |
|---|---|---|---|
| | % C | % H | % N |
| Found: | 60.72 | 4.89 | 10.67 |
| Calculated: | 60.91 | 4.96 | 10.76 |

EXAMPLE 16

(−)-2,6-dimethyl-3-carbomethoxy-4-(3-nitrophenyl)-5-{4-[1,2-dihydro-2-oxo-3-cyano-6-methyl-5(1H)-pyridyl]phenoxymethylenecarboxamidoethyloxvcarbonyl}-1,4-dihydropyridine The procedure of Example 15 was repeated using, however, the opposite enantiomer carboxylic acid of formula (IV). The title product was obtained, m.p. 209°–211° C., $[\alpha]_D^{23} = -30.8°$ (C=0.52, acetone).

| Elemental Analysis for $(C_{33}H_{31}N_5O_9 \cdot \frac{1}{2} H_2O)$: | | | |
|---|---|---|---|
| | % C | % H | % N |
| Found: | 60.89 | 4.77 | 10.69 |
| Calculated | 60.91 | 4.96 | 10.76 |

EXAMPLE 17

(±)-2,6-dimethyl-3-carbomethoxy-4-(2-chloro-3-nitrophenyl)-5-{4-[1,2-dihydro-2-oxo-3-cyano-6-methyl-5(1H)-pyridyl]phenoxymethylenecarboxamidoethyloxvcarbonyl}-1,4-dihydropyridine The procedure of Example 10 is duplicated with the exception that 2-chloro-3-nitrobenzaldehyde is used in the place of 3-nitrobenzaldehyde to yield the title product, m.p. 235°–238° C.

| Elemental Analysis for $(C_{33}H_{30}ClN_5O_9 \cdot \frac{1}{2} H_2O)$: | | | |
|---|---|---|---|
| | % C | % H | % N |
| Found: | 58.05 | 4.58 | 10.30 |
| Calculated: | 57.85 | 4.56 | 10.22 |

EXAMPLE 18

(±)-2,6-dimethyl-3-carbomethoxy-4-(2-nitrophenyl)-5-{4-[1,2-dihydro-2-oxo-3-cyano-6-methyl-5(1H)-pyridyl]phenoxymethylenecarboxamidoethyloxvcarbonyl}-1,4-dihydropyridine The procedure of Example 10 is duplicated with the exception that 2-nitrobenzaldehyde is used in the place of 3-nitrobenzaldehyde to yield the title product, m.p. 262°–264° C.

| Elemental Analysis for $(C_{33}H_{31}N_5O_9 \cdot \frac{1}{2} H_2O)$: | | | |
|---|---|---|---|
| | % C | % H | % N |
| Found: | 61.02 | 5.08 | 10.75 |

| -continued | | | |
|---|---|---|---|
| Elemental Analysis for $(C_{33}H_{31}N_5O_9 \cdot \frac{1}{2} H_2O)$: | | | |
| | % C | % H | % N |
| Calculated: | 60.91 | 4.96 | 10.76 |

EXAMPLE 19

(±)-2,6-dimethyl-3-carbomethoxy-4-(2-chlorophenyl)-5-{4-[1,2-dihydro-2-oxo-3-cyano-6-methyl-5(1H)-pyridyl]phenoxymethylenecarboxamidoethyloxvcarbonyl}-1,4-dihydropyridine The procedure of Example 10 is duplicated with the exception that 2-chlorobenzaldehyde is used in the place of 3-nitrobenzaldehyde to yield the title product, m.p. 214°–216° C.

| Elemental Analysis for $(C_{33}H_{31}ClN_4O_7 \cdot \frac{1}{2} H_2O)$: | | | |
|---|---|---|---|
| | % C | % H | % N |
| Found: | 61.51 | 4.98 | 8.59 |
| Calculated: | 61.92 | 5.04 | 8.75 |

EXAMPLE 20

(±)-2,6-dimethyl-3-carbomethoxy-4-(3-nitrophenyl)-5-{4-[2,3,4,5-tetrahydro-3-oxo-6(2H)-pyridazinyl]-(2-chlorophenoxy)propylcarbonyl}1,4-dihydropyridine A solution of 2.50 g (11.1 mmol) of the tetrahydropyranyl ether of 3-bromo-1-propanol (prepared as described in Example 7) in 10 ml of DMF is added to a mixture of 3.08 g (22.3 mmol) of anhydrous $K_2CO_3$ and 4.97 g (22.3 mmol) of 6-(3-chloro-4-hydroxyphenyl)-4,5-dihydro-3(2H)-pyridazinone (prepared as described in Eur. Pat. App. 178,189). The mixture is heated with stirring at 80° C. under $N_2$ for 3hr. The mixture is cooled, diluted with $H_2O$, and the resulting precipitate collected by filtration. The precipitate is taken up in EtOAc, dried ($MgSO_4$), filtered and the solvent removed to leave a yellow solid.

The above solid is dissolved in 70 ml of methanol and treated with about 15 mg of p-toluenesulfonic acid monohydrate. The mixture is heated 15 min at reflux, cooled, the solvent removed under vacuum, and the residue flash chromatographed on silica gel (250 ml EtOAc then 500 ml 95:5 EtOAc:MeOH) to give 7.4 g of 6-[4-(3-hydroxypropyloxy)-3-chlorophenyl]-4,5-dihydro-3(2H)-pyridazinone as a white solid. $^1$H-NMR ($d_6$-DMSO): δ 1.90 (t, 2H); 2.42 (quintuplet, 2H); 2.95 (t, 2H); 3.60 (t, 2H); 4.20 (t, 2H); 7.20 (d, 1H); 7.70 (d, 1H); 7.80 (s, 1H); 10.90 (s, 1H).

A solution of 300 mg (0.90 mmol) of (±)-2,6-dimethyl-3-carbomethoxy-4-(3-nitrophenyl)-5-carboxy-1,4-dihydropyridine, 224 mg (0.90 mmol) of 6-[4-(3-hydroxypropyloxy)-3-chlorophenyl]-4,5-dihydro-3(2H)-pyridazinone, and 11 mg (0.09 mmol) of 4-dimethylaminopyridine in 4 ml of DMF is treated with 205 mg (0.99 mmol) of DCC. The mixture is heated overnight at 80° C. under $N_2$ then cooled to RT. The precipitate of dicyclohexylurea is collected by filtration. The filtrate is diluted with EtOAc and water. The water is extracted twice with 50 ml portions of EtOAc. The combined organic phase is washed with water, dried ($MgSO_4$), filtered and the solvent removed under vacuum. The residue is purified on a preparation silica gel TLC plate (100% EtOAc) to give 243 mg of the title compound as a yellow powder, m.p. 207°–208° C.

| Elemental Analysis (for $C_{29}H_{29}ClN_4O_8$): | | | |
|---|---|---|---|
| | % C | % H | % N |
| Found: | 58.01 | 5.05 | 9.07 |
| Calculated: | 58.34 | 4.90 | 9.39 |

EXAMPLE 21

(±)-2,6-dimethyl-3-carbomethoxy-4-(2-nitrophenyl)-5-{4-[2,3,4,5-tetrahydro-3-oxo-5-methyl-6(2H)-pyridazinyl]phenoxycarbonyl}-1,4-dihydropyridine Using the procedure described in Example 3 and employing 784 mg (2.36 mmol) of (±)-2,6-dimethyl-3-carbomethoxy-4-(2-nitrophenyl)-5-carboxy-1,4-dihydropyridine, 481 mg (2.36 mmol) of 6-(4-hydroxyphenyl)-5-methyl-4,5-dihydro-3(2H)-pyridazinone, 540 mg (2.60 mmol) of DCC, and 30 mg (0.236 mmol) of 4-dimethylaminopyridine in 4 ml of DMF, 554 mg (45% yield) of the title compound is obtained as a bright yellow solid, m.p. 128°–131° C.

| Elemental Analysis (for $C_{27}H_{26}N_4O_7 \cdot 0.40\ CHCl_3$) | | | |
|---|---|---|---|
| | % C | % H | % N |
| Found: | 57.84 | 4.79 | 9.85 |
| Calculated: | 58.11 | 4.70 | 9.90 |

EXAMPLE 22

(±)-2,6-dimethyl-3-carbomethoxy-4-(2,3-dichlorophenyl)-5-{4-[2,3,4,5-tetrahydro-3-oxo-5-methyl-6(2H)-pyridazinyl]phenoxycarbonyl}-1,4-dihydropyridine Using the procedure described in Example 3 and employing 860 mg (2.41 mmol) of (±)-2,6-dimethyl-3-carbomethoxy-4-(2,3-dichlorophenyl)-5-carboxy-1,4-dihydropyridine, 493 mg (2.41 mmol) of 6-(4-hydroxyphenyl)-5-methyl-4,5-dihydro-3(2H)-pyridazinone, 550 mg (2.66 mmol) of DCC, and 30 mg (0.241 mmol) of dimethylaminopyridine in 6 ml of DMF, 781 mg (60% yield) of the title compound is obtained as a yellow solid, m.p. 145°–148° C.

| Elemental Analysis (for $C_{27}H_{25}Cl_2N_3O_5 \cdot 0.55\ CHCl_3$) | | | |
|---|---|---|---|
| | % C | % H | % N |
| Found: | 54.35 | 4.24 | 6.94 |
| Calculated: | 54.42 | 4.24 | 6.91 |

EXAMPLE 23

(±)-2,6-dimethyl-3-carbomethoxy-4-(2-chlorophenyl)-5-{4-[2,3,4,5-tetrahydro-3-oxo-5-methyl-6(2H)-pyridazinyl]phenoxymethylenecarboxamidoethyloxycarbonyl}-1,4-dihydropyridine Using the procedure described in Example 9 and employing 588 mg (1.48 mmol) of (±)-2,6-dimethyl-3-carbomethoxy-4-(2-chlorophenyl)-5-(2-aminoethoxycarbonyl)-1,4-dihydropyridine, 387 mg (1.48 mmol) of 6-(4-carboxymethoxyphenyl)-5-methyl-4,5-dihydro-3(2H)-pyridazinone, 270 μl (1.77 mmol) of diethyl cyanophosphonate, and 410 μl (2.95 mmol) of triethylamine in 4 ml of DMF, 581 mg (65% yield) of the title product is obtained as a yellow solid, m.p. 128°–130° C.

| Elemental Analysis (for $C_{31}H_{33}ClN_4O_7 \cdot \frac{1}{2}\ CHCl_3$): | | | |
|---|---|---|---|
| | % C | % H | % N |
| Found: | 56.34 | 5.01 | 8.27 |
| Calculated: | 56.57 | 5.05 | 8.38 |

PHARMACEUTICAL COMPOSITION EXAMPLES

The following examples illustrate pharmaceutical compositions with a compound of the invention.

| (A) Oral Tablets (25 mg) | for 10,000 Tablets |
|---|---|
| Compound of Example 10 | 250 g |
| Anhydrous lactose U.S.P. | 2.17 kg |
| Sta-Rx 1500 Starch | 300 g |
| Magnesium Stearate B.P. | 30 g |

The drug is sieved through a 250 μm sieve and then the 4 powders are intimately mixed in a blended and compressed between 8.5 mm diameter punches in a tabletting machine.

| (B) Oral Sustained Release Tablets (75 mg) | for 10,000 Tablets |
|---|---|
| Compound of Example 10 | 750 g |
| Cutina HR** | 0.40 kg |
| Anhydrous lactose U.S.P. | 2.06 kg |
| Magnesium Stearate B.P. | 40 g |

**Cutina HR is a grade of microfine hydrogenated castor oil supplied by Sipon Products Limited, London.

The active ingredient, Anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidized bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| (C) Oral Syrup | % w/v |
|---|---|
| Compound of Example 10 | 1.0 |
| Dilute hydrochloric acid B.P., | as required |
| Sorbitol Solution BPC | 60 v/v |
| Flavor | as required |
| Distilled water | to 100 |

The drug is dissolved in some of the water with stirring by adding gradually hydrochloric acid until the pH has fallen to 5.0. The Sorbitol Solution flavor and the rest of the water are added and the pH re-adjusted to 5.0. The syrup is clarified by filtration through suitable cellulosic filter pads.

| (D) Oral Capsules (25 mg) | for 10,000 capsules |
|---|---|
| Compound of Example 10 | 250 g |
| Sta-Rx 1500 Starch | 1700 g |
| Magnesium Stearate B.P. | 20 mg |

The drug is sieved through a 250 μm mesh sieve and is blended with the other powders. The powder is filled into No. 3 size hard gelatin capsules on a suitable filling machine.

What is claimed is:

1. A dihydropyridine selected from the group consisting of:

2,6-dimethyl-3-carbomethoxy-4-(3-nitrophenyl)-5-{4-[1,2-dihydro-2-oxo-3-cyano-6-methyl-5(1H)-pyridyl]-phenoxymethylenecarboxyamidoethyloxycarbonyl}-1,4-dihydropyridine, 2,6-dimethyl-3-carbomethoxy-4-(2-nitrophenyl)-5-{4-[1,2-dihydro-2-oxo-3-cyano-6-methyl-5(1H)-pyridyl]-phenoxymethylenecarboxyamidoethyloxycarbonyl}-1,4-dihydropyridine, 2,6-dimethyl-3-carbomethoxy-4-(2,3-dichlorophenyl)-5-{4-[1,2-dihydro-2-oxo-3-cyano-6-methyl-5(1H)-pyridyl]phenoxymethylenecarboxyamidoethyloxycarbonyl}-1,4-dihydropyridine, 2,6-dimethyl-3-carbomethoxy-4-(2-chloro-3-nitrophenyl)-5-{4-[1,2-dihydro-2-oxo-3-cyano-6-methyl-5(1H)-pyridyl]phenoxymethylenecarboxyamidoethyloxycarbonyl}-1,4-dihydropyridine, and 2,6-dimethyl-3-carbomethoxy-4-(2-chlorophenyl)-5-{4-[1,2-dihydro-2-oxo-3-cyano-6-methyl-5(1H)-pyridyl]-phenoxymethylenecarboxyamidoethyloxycarbonyl}-1,4-dihydropyridine,

* * * * *